US010758689B2

(12) United States Patent
Eilat et al.

(10) Patent No.: US 10,758,689 B2
(45) Date of Patent: Sep. 1, 2020

(54) METERED DOSE INHALER AND METHODS THEREOF

(71) Applicant: MEway Pharma Ltd., Ranana (IL)

(72) Inventors: Eran Eilat, Herzliya (IL); Joshua Altman, Tel Aviv (IL)

(73) Assignee: Sanara Tech Ltd. (IL)

( * ) Notice: Subject to any disclaimer, the term of this patent is extended or adjusted under 35 U.S.C. 154(b) by 1146 days.

(21) Appl. No.: 14/902,154

(22) PCT Filed: Jul. 3, 2014

(86) PCT No.: PCT/IL2014/050600

§ 371 (c)(1),
(2) Date: Dec. 30, 2015

(87) PCT Pub. No.: WO2015/001561

PCT Pub. Date: Jan. 8, 2015

(65) Prior Publication Data

US 2016/0213864 A1 Jul. 28, 2016

Related U.S. Application Data

(60) Provisional application No. 61/842,446, filed on Jul. 3, 2013.

(51) Int. Cl.
*A61M 15/00* (2006.01)
*A61M 11/00* (2006.01)
(Continued)

(52) U.S. Cl.
CPC ........ *A61M 15/009* (2013.01); *A61M 11/001* (2014.02); *A61M 11/007* (2014.02);
(Continued)

(58) Field of Classification Search
CPC .. A61M 15/009; A61M 11/02; A61M 11/002; A61M 11/007; A61M 11/008; A61M 11/001
See application file for complete search history.

(56) References Cited

U.S. PATENT DOCUMENTS

| | | | |
|---|---|---|---|
| 3,672,545 | A | 6/1972 | Marand |
| 3,733,010 | A | 5/1973 | Riccio |
| 3,788,525 | A | 1/1974 | Thornton et al. |
| 3,856,185 | A | 12/1974 | Riccio |

(Continued)

FOREIGN PATENT DOCUMENTS

| | | | |
|---|---|---|---|
| WO | 9007351 | A1 | 7/1990 |
| WO | 9921659 | A1 | 5/1999 |

(Continued)

OTHER PUBLICATIONS

International Search Report for PCT/IL2014/050600 dated Sep. 22, 2014.

*Primary Examiner* — Samchuan C Yao
*Assistant Examiner* — Margaret M Luarca
(74) *Attorney, Agent, or Firm* — Burns & Levinson, LLP; Joseph M. Maraia

(57) ABSTRACT

A process and a metered dose inhaler, comprising: an air actuator comprising at least one inlet of liquefied gas (LG), at least one air outlet, at least one first LG-expanding volume and at least one second air-containing volume, the first and second volumes are effectively separated by means of a LG-blocking member; a container with an LG source; said container is in a fluid connection with said LG-expanding volume via the at least one LG inlet; The air actuator is facilitating a metered dose airflow by allowing the expansion of said LG in said at least one LG-expanding volume from its condensed liquid phase to its expanded gas phase. The expansion of said LG facilitates the compression of the air within said at least one air-containing volume, such that
(Continued)

a metered dose LG-free air flow is inhalable via at least one air outlet.

24 Claims, 12 Drawing Sheets

(51) Int. Cl.

| | |
|---|---|
| ***A61M 11/02*** | (2006.01) |
| ***A61M 16/20*** | (2006.01) |
| ***A61M 11/06*** | (2006.01) |

(52) U.S. Cl.
CPC ........... *A61M 11/008* (2014.02); *A61M 11/02* (2013.01); *A61M 11/06* (2013.01); *A61M 15/0003* (2014.02); *A61M 15/0065* (2013.01); *A61M 16/201* (2014.02); *A61M 2202/02* (2013.01); *A61M 2202/03* (2013.01); *A61M 2202/0468* (2013.01); *A61M 2202/064* (2013.01); *A61M 2205/0272* (2013.01); *A61M 2205/07* (2013.01)

(56) References Cited

U.S. PATENT DOCUMENTS

| | | | | |
|---|---|---|---|---|
| 3,926,343 | A | 12/1975 | Kleiner | |
| 4,017,007 | A | 4/1977 | Riccio | |
| 4,263,907 | A * | 4/1981 | Lindsey | A61M 16/16 128/200.18 |
| 4,949,715 | A | 8/1990 | Brugger | |
| 5,248,493 | A | 9/1993 | Brown | |
| 5,893,515 | A | 4/1999 | Hahn et al. | |
| 6,143,277 | A * | 11/2000 | Ashurst | A61M 15/009 424/45 |
| 2005/0247305 | A1 | 11/2005 | Zierenberg et al. | |
| 2006/0201499 | A1 | 9/2006 | Muellinger et al. | |
| 2007/0282276 | A1 | 12/2007 | Boeck et al. | |
| 2014/0283831 | A1 * | 9/2014 | Foote | A61M 16/026 128/204.19 |

FOREIGN PATENT DOCUMENTS

| | | | |
|---|---|---|---|
| WO | 2004011068 | A1 | 2/2004 |
| WO | 2005060480 | A2 | 7/2005 |
| WO | 2013098334 | A1 | 7/2013 |

* cited by examiner

METERED DOSE INHALER AND METHODS THEREOF

CROSS REFERENCE TO RELATED APPLICATIONS

This application is a U.S. national stage application under 35 U.S.C. 371 of co-pending International Application No. PCT/IL2014/050600, filed ON Jul. 3, 2014. The International Application, in turn, claims priority to U.S. Provisional Application No. 61/842,446, filed on Jul. 3, 2013. The entire contents of the above applications are incorporated herein by reference for all purposes.

FIELD OF THE INVENTION

The present invention is related to an air pressure-operated metered dose inhaler. More particularly, the invention pertains to an air pressure-operated metered dose inhaler which comprises an air actuator adapted for releasing a flow of compressed air at such time as a predetermined liquefied gas (LG) pressure has been reached, and to methods thereof.

BACKGROUND OF THE INVENTION

Among the many devices which are adapted to deliver gas, fluid or further medicaments, to the lung, metered inhalers are widely used. Several patents describe metered inhalers for delivering gas, fluid or medicaments.

U.S. Pat. No. 4,017,007 discloses an air pressure-operated dispenser for spraying a single dose of a fluent material of liquid or powder form. The dispenser has a single dose container having a compressed air inlet opening and a closable discharge orifice and means for closing the discharge orifice in a non-dispensing position of the dispenser. An air-compressing piston pump having a compressed air outlet from a compression space thereof is further provided on the dispenser at the junction of the inlet opening and the compressed air outlet.

The inlet opening of the single dose container is joined to the compressed air outlet of the compression space and valve means is provided on the piston pump for releasing a flow of compressed air.

U.S. Pat. No. 5,893,515 discloses a device for generating a spray of mist or fine droplets includes a spinning rotor within a mist chamber. The rotor has inner walls which taper conically outwardly from the open bottom of the rotor to a hole near the top of the rotor.

Liquid is pumped by a finger actuated pump from a cartridge module into a bowl surrounding the bottom end of the rotor. The spray is created as the liquid is formed into droplets as it passes through the hole in the rotor under centrifugal force.

PCT patent application No. 2004011068 discloses a medicament dispenser device for use in the delivery of a combination medicament product. The dispenser comprises a first medicament container for containing a first medicament component, a first release means for releasing the contents of said first medicament container, at least one medicament container for containing at least one further medicament component, and at least one release means for releasing the contents of at least one medicament. The first medicament component is kept separate from the at least one further medicament component until the point of release thereof for delivery in combination. The dispenser additionally comprises an electronic control system for controlling the release of contents from the medicament container.

EP patent application No. 1689474 discloses an inhaler which comprises a compressed gas, in a first chamber which is in communication with an equalization chamber having pressure lower than the pressure of the gas in the first compressed chamber and having a drug storage chamber which is detachably coupled to the equalization chamber operable such that a portion of the compressed gas from the equalization chamber fluidizes and aerosolizes the drug to produce a drug cloud and which can then be injected into a spacer where it can be inhaled by a user.

PCT application No. 1999021659 discloses a device and a method of reducing the droplet size of a composition sprayed from an aerosol spray device comprising a compressed gas propellant, which method comprises imparting a unipolar charge to the liquid droplets by double layer charging during the spraying of the liquid droplets from the aerosol spray device, the unipolar charge being at a level such that the droplets have a charge to mass ratio of at least +/−1×10<−4> C/kg.

The above-described devices are electrically powered, less portable or provide long treatment time. It therefore remains a long felt and unmet need to provide novel means and methods for an inhaler device which generates and delivers a dose of gas, fluid or a mixture thereof in a more effective and short term manner.

SUMMARY OF THE INVENTION

It is an object of the present invention to disclose a novel metered dose inhaler. This inhaler comprises an air actuator comprising at least one inlet of liquefied gas (LG), at least one air outlet, at least one first LG-expanding volume and at least one second air-containing volume, the first and second volumes are effectively separated by means of an LG-blocking member, a container with an LG source; the container is in a fluid connection with the LG-expanding volume via the at least one LG inlet; wherein the air actuator is facilitating a metered dose airflow by allowing the expansion of the LG in the at least one LG-expanding volume from its condensed liquid phase to its expanded gas phase, and further wherein the expansion of the LG facilitates the compression of the air within the at least one air-containing volume, such that a metered dose LG-free air flow is inhalable via the at least one air outlet.

It is another object of the present invention to disclose a metered dose inhaler which comprises (a) a liquefied gas (LG) source, (b) a volume adapted to contain LG, the volume fluidly connected to the LG source, (c) an air-containing volume, (d) an air outlet fluidly connected to the air-containing volume and, (e) an air actuator separating the LG-containing volume from the air-containing volume; the air actuator is adapted to release a flow of compressed air through the air outlet at such time as a predetermined LG pressure has been reached in the volume adapted to contain LG; wherein the LG and the air remain separate at all times; further wherein the compressed air is released at a predetermined pressure.

It is another object of the present invention to provide the inhaler as defined in any of the in any of the above, wherein the air actuator is selected from a group consisting of a piston pump, a turbine, a rotor, an inflatable membrane and a combination thereof.

It is another object of the present invention to provide the inhaler as defined in any of the above, wherein the inhaler additionally comprising a valve means in communication with the air actuator; the valve means comprising at least one control valve having a single state and at least two directing valves configured to identify and control the actuator movement, position and direction.

It is another object of the present invention to provide the inhaler as defined in any of the above, wherein the at least two directing valves are based on ferromagnetic mechanism.

It is another object of the present invention to provide the inhaler as defined in any of the above, wherein the inhaler additionally comprising a valve in a fluid connection with the LG source.

It is another object of the present invention to provide the inhaler as defined in any of the above, wherein additionally comprising an energy source selected from the group consisting of: electric motor, electric linear actuator, electromagnetic solenoid based actuator, spring operated mechanism, hydraulic pump, compressed gas (CG), flywheel, steam engine, carnot machine, stirling cycle and a combination thereof.

It is another object of the present invention to provide the inhaler as defined in any of the above, wherein the air actuator is adapted for controlling the flow of the compressed air after build-up of a predetermined pressure.

It is another object of the present invention to provide the inhaler as defined in any of the above, wherein the inhaler additionally comprising an air inlet.

It is another object of the present invention to provide the inhaler as defined in any of the above, wherein the inhaler additionally comprising an LG outlet.

It is another object of the present invention to provide the inhaler as defined in any of the above, wherein the LG-expanding volume contains a first compressed LG compressed between about 20 and about 200 psig, and the air containing volume contains compressed air compressed between about 3 and about 10 psig.

It is another object of the present invention to provide the inhaler as defined in any of the above, wherein the membrane, when inflated by the LG source, compresses air flow via the air outlet.

It is another object of the present invention to provide the inhaler as defined in any of the above, wherein the membrane is configured as a diaphragm-like shape or a condom-like shape.

It is another object of the present invention to provide the inhaler as defined in any of the above, wherein the inhaler additionally comprising a mist nozzle in a fluid connection with the air outlet.

It is another object of the present invention to provide the inhaler as defined in any of the above, wherein the LG is selected from the group consisting of liquefied petroleum gas (LPG), propane, butane and a combination thereof.

It is another object of the present invention to provide the inhaler as defined in any of the above, wherein the inhaler additionally comprising a medicament metering mechanism comprising a medicament chamber and a medicament metering valve, the valve is in a fluid connection with the medicament chamber.

It is another object of the present invention to provide the inhaler as defined in any of the above, wherein the medicament is in a form selected from the group consisting of solid form, gas form, liquid form and a combination thereof.

It is another object of the present invention to provide the inhaler as defined in any of the above, wherein the medicament is administrated in a manner selected from the group consisting of: systemic administration via the patient's lungs, topical administration and a combination thereof.

It is another object of the present invention to provide the inhaler as defined in any of the above, wherein the inhaler is configured for spraying one or more members of a group consisting of gas materials, liquid materials, fine particles, powder materials and a mixture thereof.

It is another object of the present invention to provide the inhaler as defined in any of the above, wherein the inhaler is portable and handheld.

It is another object of the present invention to provide the inhaler as defined in any of the above, wherein the inhaler is used for treating asthma, chronic obstructive pulmonary disease (COPD) and other respiratory diseases and conditions.

It is another object of the present invention to disclose a nozzles system for dispensing a consecutively dose of a medicament in the form of a mist, comprising:

a. an inhaler comprising an air actuator comprising at least one inlet of liquefied gas (LG), at least one air outlet, at least one first LG-expending volume and at least one second air-containing volume, the first and second volumes are effectively separated by means of an LG-blocking member;
b. a container with a LG source; the container is in a fluid connection with the LG-expending volume via the at least one LG inlet and a spring means in communication with the air actuator;
c. at least two nozzles in fluid communication with the air outlet;

wherein the nozzles are venturi nozzles arrange in a predetermined angle such that the droplet size of a medication dispersed from the inhaler is in a range of about 1μ to about 5μ;

It is another object of the present invention to provide the nozzles system according as defined in any of the above, wherein nozzles are configured to disperse at least 2.5 ml of the medication in approximately 2 minutes.

It is another object of the present invention to provide the nozzles system according as defined in any of the above, wherein the at least two nozzles are interconnected in a vertically or to each other.

It is another object of the present invention to provide the nozzles system according as defined in any of the above, wherein the nozzle type is selected from the group consisting of laskin nozzle, annular flow high velocity, colliding streams nozzle, additive energy nozzles, swirl nozzle and a combination thereof.

It is another object of the present invention to provide the nozzles system according as defined in any of the above, wherein the nozzles are with a diameter configured to disperse a droplets size less than 5μ vs the released dose or medication.

It is another object of the present invention to provide the nozzles system according as defined in any of the above, wherein the nozzles are configured with a diameter of about 0.5 mm to provide a droplets distribution of more than 70% of the medication.

It is another object of the present invention to provide the nozzles system according as defined in any of the above, wherein the nozzles are with a diameter of about 0.5 mm to disperse a droplets size is in a range of about 2μ to about 3μ

It is another object of the present invention to provide the nozzles system according as defined in any of the above, wherein the at least two nozzles interconnected in a vertical angle generate a mist of about 80% droplets smaller than 3μ

It is another object of the present invention to provide the nozzles system according as defined in any of the above, wherein the at least two nozzles interconnected in a vertical angle generate a mist of about 90% droplets smaller than 5μ

It is another object of the present invention to disclose a method of introducing a dose from a metered dose inhaler, comprising steps of: providing a metered dose inhaler with an air actuator; providing at least one inlet of liquefied gas (LG), at least one air outlet, at least one first LG-expanding volume and at least one second air-containing volume, providing the first and second volumes separated by means of an LG-blocking member; a container with an LG source; providing the container in a fluid connection with the LG-expanding volume via the at least one LG inlet and, then releasing the LG directly to the actuator;

wherein the method of releasing the LG directly to the actuator further comprises steps of facilitating metered dose airflow by an air actuator thereby allowing the expansion of the LG in the LG-expanding volume from its condensed liquid phase to its expanded gas phase, and further wherein the method additionally comprising steps of facilitating the compression of the air within the air-containing volume by the expansion of the LG, such that a metered dose LG-free air flow is inhaled via the air outlet.

It is another object of the present invention to provide the method as defined in any of the above, wherein the method additionally comprising step of selecting the air actuator from a group consisting of a piston pump, a rotor, a turbine, an inflatable membrane and a combination thereof.

It is another object of the present invention to provide the method as defined in any of the above, wherein the method additionally comprising steps of configuring the membrane as a diaphragm or condom.

It is another object of the present invention to provide the method as defined in any of the above, wherein the method additionally comprising step of providing a mist nozzle in a fluid connection with the inhaler.

It is another object of the present invention to provide the method as defined in any of the above, wherein the method additionally comprising step of selecting the LG from a group consisting of liquefied petroleum gas (LPG), propane, butane and a mixture thereof.

It is another object of the present invention to provide the method as defined in any of the above, wherein the method additionally comprising step of providing a medicament selected from a group consisting of solid form, gas form, liquid form and a mixture thereof.

It is another object of the present invention to provide the method as defined in any of the above, wherein the method additionally comprising step of configuring the inhaler for spraying at least one dose form selected from the group consisting of a gas material, a flow material, fine particles, a liquid material, a powder material and a mixture thereof.

It is another object of the present invention to provide the method as defined in any of the above, wherein the method additionally comprising step of providing the inhaler as a portable and handheld device.

It is another object of the present invention to provide the method as defined in any of the above, wherein the method additionally comprising step of introducing the inhaler to the topical system or the systemic system via the patient's lungs.

It is another object of the present invention to disclose a method of treating respiration disorders in a patient which comprises use by the patient of a metered dose inhaler of the present invention.

It is another object of the present invention to disclose a device operative in a method of dispersing a dose, comprising steps of: providing a metered dose inhaler with an air actuator comprising at least one inlet of liquefied gas (LG), at least one air outlet, at least one first LG-expanding volume and at least one second air-containing volume, the first and second volumes are effectively separated by means of an LG-blocking member; providing a container with an LG source; the container is in a fluid connection with the LG-expanding volume via the at least one LG inlet; releasing the LG directly to the actuator;

wherein the step of releasing the LG directly to the actuator is followed by an additional step of facilitating a metered dose airflow by the air actuator, thereby allowing the expansion of the LG in the LG-expanding volume from its condensed liquid phase to its expanded gas phase, and further wherein the step is followed by an additional step of facilitating the compression of the air within the air-containing volume by the expansion of the LG, such that a metered dose LG-free air flow is inhaled via the air outlet.

It is another object of the present invention to disclose a metered dose inhaler for improving medicament's alveolar deposition comprising: at least one inlet of liquefied gas (LG) communicating with at least one first volume for LG-expansion; at least one second volume for containing a medicament, the second volume in fluid connection with at least one medicament outlet; an air actuator configured for moving air and the medicament towards patient's respiratory tract; and a container with a liquefied LG source, the container is in fluid connection with the first volume, where the LG is allowed to gasify, via the at least one LG inlet; wherein the air actuator comprises an LG-blocking member separating the first volume where LG is in liquid phase and the second volume where the LG is in it gas phase; and wherein the LG-blocking member moveable towards the medicament outlet by means of a pressure exerted by the LG-phase transition, thereby emitting effective measure of the medicament.

It is another object of the present invention to provide the inhaler as defined in any of the above, wherein the air actuator is selected from a group consisting of a piston pump, a turbine, a rotor, an inflatable membrane and a combination thereof.

It is another object of the present invention to provide the inhaler as defined in any of the above, wherein the outlet is provided with an orifice having a diameter of about 0.2 mm to about 0.9 mm, operably configured to emit effective measure of the medicament having average particles size equal to or less than 5 μm.

It is another object of the present invention to provide the inhaler as defined in any of the above, wherein the LG is with a pressure operably configured to emit effective measure of the medicament having average particles size equal to or less than 5 μm.

It is another object of the present invention to provide the inhaler as defined in any of the above, wherein the second volume is with a volume operably configured to emit effective measure of the medicament having average particles size equal to or less than 5 μm.

It is another object of the present invention to provide the inhaler as defined in any of the above, wherein the LG blocking member is with a speed of movement operably configured to emit high medicament quantity having average particles size equal to or less than 5 μm.

It is another object of the present invention to disclose a method of improving medicament's alveolar deposition characterized by the following steps:

providing a metered dose inhaler for improving medicament's alveolar deposition with at least one inlet of liquefied gas (LG) communicating with at least one first volume for LG-expansion;

at least one second volume for containing a medicament, the second volume in in fluid connection with at least one medicament outlet; an air actuator configured for moving air and the medicament towards patient's respiratory tract; and a container with a liquefied LG source, the container is in fluid connection with the first volume, where the LG is allowed to gasify, via the at least one LG inlet;

releasing the liquefied LG directly to the actuator, thereby gasifying the LG and actuating the actuator; and facilitating the flow of an effective measure of the medicament towards the alveoli via patient's respiratory tract.

It is another object of the present invention to provide the method as defined in any of the above, wherein the method additionally comprising step of reducing, by means of the medicament dispensing nozzle, the average particle size of the medicament outflow to value being equal to or less than 5 μm, followed by a step of facilitating the flow of the medicament.

It is another object of the present invention to provide the method as defined in any of the above, wherein the method additionally comprising step of selecting the air actuator from a group consisting of a piston pump, a rotor, a turbine, an inflatable membrane and a combination thereof.

It is another object of the present invention to disclose a standard of care protocol for increasing both (i) deposition of a medicament and (ii) kinetics per internal surface area of the alveoli to the respiratory tract by means of a metered dose inhaler, the protocol characterized by providing a metered dose inhaler for improving medicament's alveolar deposition with at least one inlet of liquefied gas (LG) communicating with at least one first volume for LG-expansion; at least one second volume for containing a medicament, the second volume in in fluid connection with at least one medicament outlet;

an air actuator configured for moving air and the medicament towards patient's respiratory tract; and a container with a liquefied LG source, the container is in fluid connection with the first volume, where the LG is allowed to gasify, via the at least one LG inlet; and facilitating the flow towards the respiratory tract of a patient, by the air actuator, an LG-free meter-dose medicament comprising a medicament, wherein the inhaled medicament is of an average particles size equal to or less than 5 μm, thereby absorbing more than 50% of the medicament in the alveoli.

It is another object of the present invention to provide the standard of care protocol as defined in any of the above, wherein the standard of care protocol additionally comprising step of selecting the air actuator from a group consisting of a piston pump, a rotor, a turbine, an inflatable membrane and a combination thereof.

BRIEF DESCRIPTION OF THE DRAWINGS

In the following description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention. The present invention may be practiced according to the claims without some or all of these specific details. For the purpose of clarity, technical material that is known in the technical fields related to the invention has not been described in detail so that the present invention is not unnecessarily obscured. In the accompanying drawing:

DETAILED DESCRIPTION OF THE PREFERRED EMBODIMENTS

The present invention have been defined specifically to provide device, means and method for an air pressure-operated inhaler for spraying at least one dose form, comprising: a gaseous propellant, actuator means adapted to release a flow of compressed air after a predetermined liquefied gas (LG) pressure has been reached, and, an air outlet. The actuator means operated by the activated liquefied gas (LG) pressure in order to compress air via the air outlet. The actuator means builds up a pressure on the air delivery side for causing metered dose airflow.

Figure 1A:
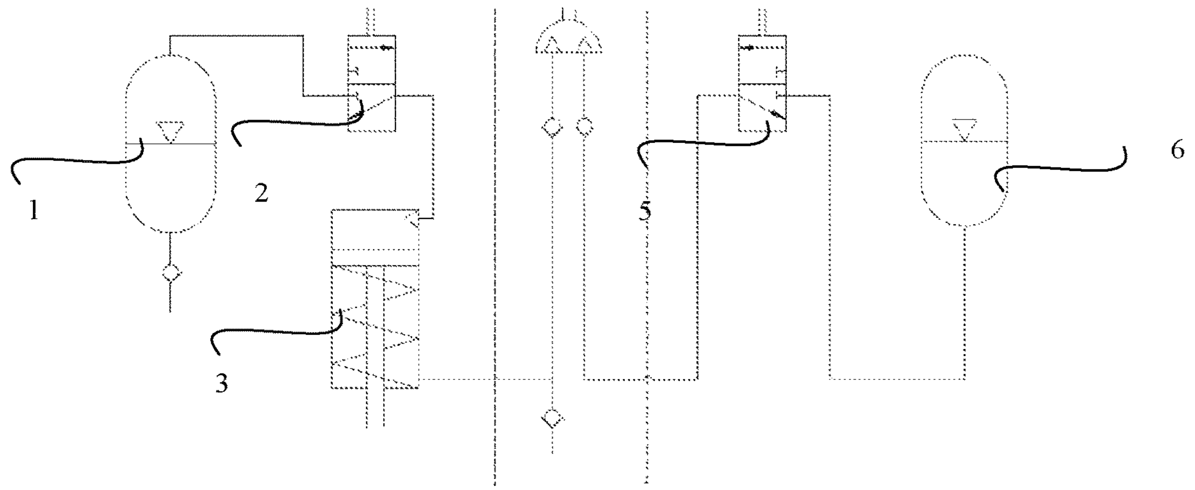
FIGS. 1A-C present a schematic view of metered dose inhaler system of the present invention.
Figure 1B:
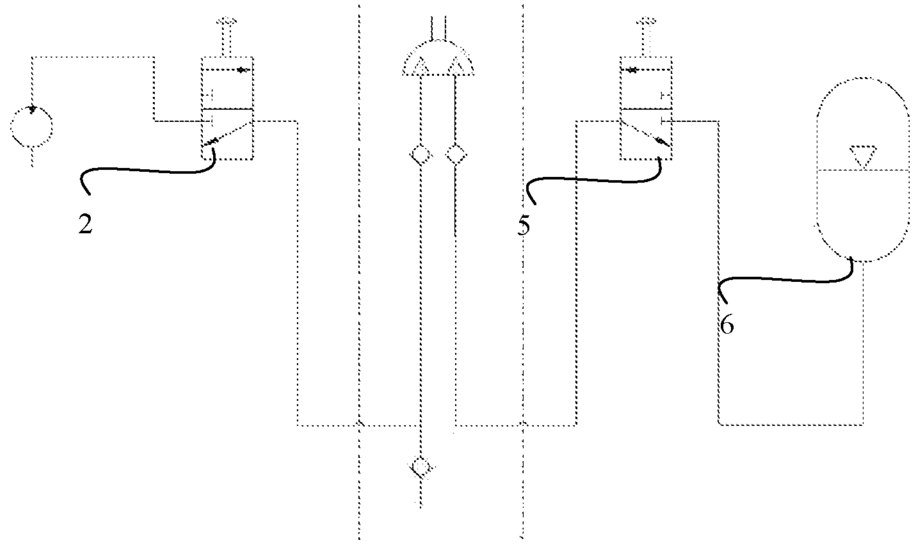
Figure 1C:
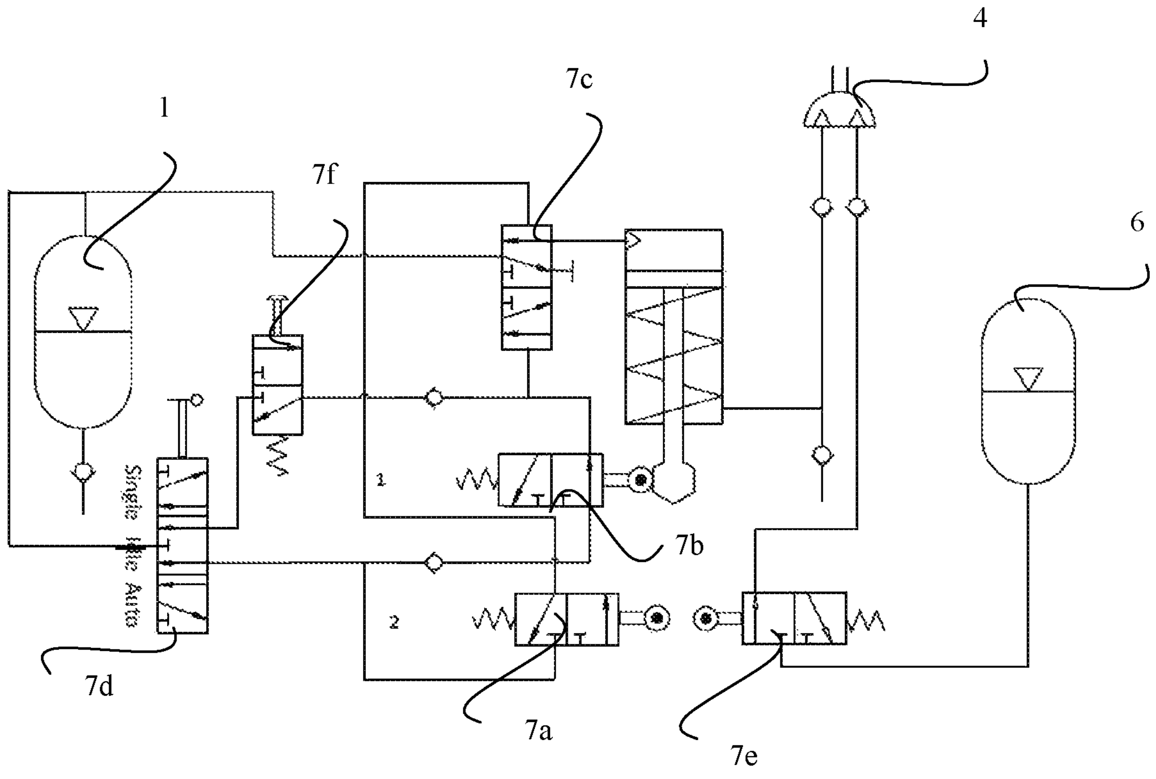

Reference is now made to FIGS. 1*a-c* which illustrate a schematic view of metered dose inhaler system, comprising: an air actuator comprising at least one inlet of liquefied gas (LG), at least one air outlet, at least one first LG-expanding volume and at least one second air-containing volume. The first and second volumes are effectively separated by means of an LG-blocking member. The inhaler further comprises a container with LG source. The container is in a fluid connection with LG-expanding volume via at least one LG inlet. The air actuator is facilitating the metered dose airflow by allowing the expansion of the LG in at least one LG-expanding volume from its condensed liquid phase to its expanded gas phase. Furthermore the expansion of the LG facilitates the compression of the air within the at least one air-containing volume, such that a metered dose LG-free air flow is inhalable via the at least one air outlet.

The present invention further provides an air pressure-operated inhaler for spraying at least one dose form, comprising: (a) a liquefied gas (LG) source 1; (b) a volume adapted to contain LG, the volume is fluidly connected to the LG source, (c) an air-containing volume, (d) at least one air outlet fluidly connected to air-containing volume and, (e) actuator means 3 separating the LG-containing volume from the air-containing volume. The actuator means is adapted to release a flow of compressed air through the air outlet at such time as a predetermined LG pressure has been reached in the volume adapted to contain LG.

The LG and the air remain separate at all times. Furthermore the compressed air is released at a predetermined pressure. The airflow released from the inhaler outlet depended upon differential pressure gauges between the one LG-expanding volume and the air-containing volume separated by means of an LG-blocking member.

In another embodiment of the present invention the inhaler comprises an orifice having a diameter for emitting effective measure of about 0.1 ml to about 3 ml of medicament in less than about 6 minutes.

The LG-expanding volume is adapted for containing a compressed LG at a first pressure. The air containing volume may be in a selective communication with LG-expanding volume. The air containing volume is adapted for containing a compressed air at a second pressure less than the first pressure. Both of the volumes are cooperating so as to yield a second pressure of the compressed air within the air containing volume.

The LG-expanding volume contains a compressed LG compressed between about 20 to about 200 psig, and the air containing volume contains compressed air compressed between about 3 to about 10 psig.

As used herein the term "about" denotes ±25% of the defined amount or measure or value.

Furthermore, a differential pressure gauge is further created between the outlet and inlet ports, each connected to one of the volume portions whose pressure is to be monitored.

The inhaler may further comprise a system or mechanism for delivering a medicament, the system may comprise an additionally medicament chamber 6 for loading a medicament and a medicament metering valve 5 for releasing the medicament from the chamber. The medicament metering valve is in fluid connection with the medicament chamber. The medicament metering valve is in charged on delivering a specific amount of medicament to the patients lungs. The medicament may be delivered in a form of a short burst of aerosolized medicine that is inhaled by the patient.

In another embodiment of the present invention, the inhaler is further configured with an LG-blocking member to prevent contamination between the air and/or medicament within the air containing volume and the LG within LG-expanding volume. The LG-blocking member may be an integral part of the actuator or an independent unit such as slidable rod-like for separating the two volumes and for better sealing.

The inhaler of the present invention may further comprise a mist nozzle, such that the compressed LG pushes a predetermined amount of a medicament through a nozzle generating an aerosol for inhalation. The medicament may be further admixed with the compressed air creating a mist to be dispersed from the mist nozzle. The mist nozzle may comprise a plurality of apertures having different diameter for controlling the particles size diameter of a dispersed medicament.

FIG. 1*c* further illustrates the inhaler system comprising valve means 7*a*-7*f* designated herein in a predefined arrangement adjacent to the inhaler LG inlet having high pressure LG supplied directly to the valve so that when at least one of valve is opened in response to system determinations, the gas at high pressure can be substantially immediately delivered at a steady state of flow and pressure to the inhaler unit to nearly or substantially instantaneously begin nebulization producing the proper distribution range and of particle sizes at a desired density. The valve means further comprising at least one control valve 7*d*,7*f* and at least three directing valves 7*a*,7*b*,7*c*. The control valve 7*d* comprises a single state and may further comprise an idle state and an automatic (auto) state for activating the inhaler. The directing valves 7*a*,7*b*,7*c* control and further monitor the actuator movement in the axial direction whilst LG is released by the LG-directing valve 7*c* to the LG-expanding volume and further forcing the actuator to downward position. The directing valves 7*b*,7*a* are based upon ferromagnetic mechanism such that when the actuator is forced to a downward position valve 7*b* pulls down the actuator and when the actuator reaches to valve 7*a* the actuator is released back to its rest position. The valve means further comprising a medication metering valve 7*e* which controls the medication release from the medication container 15 to a nozzles system.

The present invention further provides a device operative in a method of dispersing a dose, comprising steps of providing a metered dose inhaler with an air actuator comprising at least one inlet of liquefied gas (LG), at least one air outlet, at least one first LG-expanding volume and at least one second air-containing volume. The first and second volumes are effectively separated by means of an LG-blocking member; providing a container with an LG source.

The container is in a fluid connection with the LG-expanding volume via at least one LG inlet, releasing the LG directly to the actuator, wherein the step of releasing the LG directly to the actuator additionally comprising step of facilitating metered dose airflow by air actuator thereby allowing the expansion of the LG in the LG-expanding volume from its condensed liquid phase to its expanded gas phase, and further wherein the method additionally comprising step of facilitating the compression of the air within the air-containing volume by the expansion of the LG, such that a metered dose LG-free air flow is inhaled via the air outlet.

In another embodiment of the present invention, the LG-blocking member is moveable towards the medicament outlet by means of a pressure exerted by the LG-phase transition, thereby emitting effective measure of a medicament.

The term "effective measure" of a medicament refers hereinafter to a medicament dose to be delivered towards patient's respirator tracks, wherein the dose is sufficient for curing the patient according to a predefined treatment protocol. It is well within the scope of the invention, where effective measure ranges from 1 microgram to 1 gram, It is further in the scope of the invention, where effective measure of the medicaments is provided when characterized by an average particles size of less than about 5 μm. Additional or alternatively, it is in the scope of the invention, where effective measure of the medicaments is characterized by a homogeneous medicament, i.e., one or more medicaments introduced to patient's respiratory tract by air carrier, and not another carrier, such as a carbon-containing liquefied gas (carbon dioxide, butane, propane etc.). Additional or alternatively, it is in the scope of the invention, where effective measure of the medicaments is a minimal dose useful for providing enhanced medicament absorption and kinetics per internal surface area of patient's alveoli. Additional or alternatively, it is in the scope of the invention, where effective measure of the medicaments is characterized by an average particles size (APS) μm, wherein the inhaled medicament is sized equal or less the APS to absorbed more than 50% per internal surface area in the alveoli.

According to an embodiment of the invention the average particles size is in a range 0.75 μm≤APS≤5.0 μm.

In another embodiment of the present invention, the air outlet may be provided with an orifice having a diameter of about 0.2 mm to about 0.9 mm. The air outlet may be provided with an orifice operably configured to emit effective measure of the medicament having average particles size between one or more of the following rangers: 0.5-7.5

μm, 0.5-2.5 μm, 2.5-5.0 μm or 5.0-7.5 μm. The inhaler may further provide droplets distribution having a diameter equal to or less than 5 μm.

Additional or alternatively, the LG is with a pressure operably configured to emit effective measure of the medicament having average particles size equal to or less than 5 μm. Additional or alternatively, the second air-containing volume is with a volume operably configured to emit effective measure of the medicament having average particles size equal to or less than 5 μm.

Additional or alternatively, the LG blocking member is with a speed of movement operably configured to emit high medicament quantity having average particles size equal to or less than 5 μm.

The present invention further provides a method of improving medicament's alveolar deposition characterized by the following steps: providing a metered dose inhaler for improving medicament's alveolar deposition with at least one inlet of liquefied gas (LG) communicating with at least one first volume for LG-expansion; at least one second volume for containing a medicament, the second volume in in fluid connection with at least one medicament outlet; an air actuator configured for moving air and the medicament towards patient's respiratory tract; and a container with a liquefied LG source, the container is in fluid connection with the first volume, where the LG is allowed to gasify, via the at least one LG inlet;

The method additionally comprising the step of releasing the liquefied LG directly to the actuator, thereby gasifying the LG and actuating the actuator and facilitating the flow of an effective measure of the medicament towards the alveoli via patient's respiratory tract.

The method additionally comprising step of reducing, by means of the medicament dispensing nozzle, the average particle size of the medicament outflow to a diameter value being equal to or less than 5 μm, followed by a step of facilitating the flow of the medicament.

It is another object of the present invention to provide a standard of care protocol for increasing both (i) deposition of a medicament and, (ii) kinetics per internal surface area of the alveoli via the respiratory tract by means of a metered dose inhaler. The protocol is characterized by providing a metered dose inhaler for improving medicament's alveolar deposition with at least one inlet of the liquefied gas (LG) communicating with at least one first volume for LG-expansion; at least one second volume for containing a medicament, the second volume is in fluid connection with at least one medicament outlet; an air actuator configured for moving air and the medicament towards patient's respiratory tract; and a container with a liquefied LG source, the container is in fluid connection with the first volume, where the LG is allowed to gasify, via the at least one LG inlet; and facilitating the flow towards the respiratory tract of a patient, by the air actuator, an LG-free meter-dose medicament comprising a medicament, wherein the inhaled medicament is of an average particles size equal to or less than 5 μm, thereby absorbing more than 50% of the medicament in the alveoli. The standard of care protocol additionally comprising step of selecting the air actuator from a group consisting of a piston pump, a rotor, a turbine, an inflatable membrane, a spring and a combination thereof.

According to one embodiment of the present invention, the medicament may be selected from granular matter, a drug sized to form fine particles, powder, sol, gel, sol-gel, glass, encapsulated matter, milled composition or any combination thereof. Alternatively or additionally, the medicament may be utilized in a liquid phase. In such a case, the fluid is selected in a non-limiting manner from water miscible compositions, water immiscible compositions, emulsions, extracts, dispersions, suspensions, vasiculated solutions, aggregated phases or any combination thereof. It is according to another embodiment of the present invention wherein the fluid or medicament is selected in a non-limiting manner from at least one of the group of Braochodilators, especially sympatic mimetics, alfa antagonists, anti cholinergics; nasal decongestants, such as pseudoehedrines, ephedrines; steroids; anti histamines; anti prostaglandins, alternative or homeopathic medicaments; vaso constrictors; local anesthetics; mast cell stabilizers; antibiotics, such as biocides, fungicides etc; pleasant odor; pheromones; hormone treatments, such as ADH, insulin, growth hormones; vapors, humidifiers; drying compositions; hot or cold vapors; hyper-, iso- or hypotonic vapors or any combination thereof, or decongestants, essential oils, volatile compounds, etheric oils, terepenes, terpanols and either water miscible or water-immiscible extracts, especially oils or extracts.

The inhaler can be adapted for treating asthma, chronic obstructive pulmonary disease (COPD) and other respiratory diseases and conditions. The medicament may be in a form selected from a group consisting of solid form, gas form, liquid form and combination thereof.

According to one embodiment of the present invention, the inhaler may further be adapted to deliver medicament for treating chronic inflammatory diseases such as asthma, as presented in table 1 below:

| Category | Purpose | Medicament types |
|---|---|---|
| Long-term asthma control medicaments | Taken regularly to control chronic symptoms and prevent asthma attacks - the most important type of treatment for most people with asthma | Inhaled corticosteroids<br>Leukotriene modifiers<br>Long-acting beta agonists (LABAs)<br>Theophylline<br>Combination inhalers that contain both a corticosteroid and a LABA |
| Quick-relief medicaments (rescue medicaments) | Taken as needed for rapid, short-term relief of symptoms - used to prevent or treat an asthma attack | Short-acting beta agonists such as albuterol<br>Ipratropium (Atrovent)<br>Oral and intravenous corticosteroids (for serious asthma attacks) |
| Medicaments for allergy-induced asthma | Taken regularly or as needed to reduce your body's sensitivity to a particular allergy-causing substance (allergen) | Allergy shots (immunotherapy)<br>Omalizumab (Xolair) |

Other medicaments may further be adapted, selected from the group consisting of: Bronchodilators Short-acting bronchodilators (including: Anticholinergics (such as ipratropium), Beta2-agonists (such as albuterol and levalbuterol)), a combination of the two Long-acting bronchodilators, (including: Anticholinergics (such as tiotropium), Beta2-agonists (such as salmeterol, formoterol, and arformoterol)), Phosphodiesterase-4 (PDE4) inhibitors, Corticosteroids (such as prednisone), Expectorants, (such as guaifenesin (Mucinex)), Methylxanthines.

Other medicaments may further be adapted for treating Chronic obstructive pulmonary disease (COPD), selected from the group consisting of: Aclidinium inhalation, aclidinium/formoterol inhalation, AM211, AZD1981 (CRTh2 receptor antagonist), AZD 2115 (MABA), AZD 2423 (CCR2b antagonist), AZD3199 (iLABA), AZD5069 (CXCR2), AZD5423, AZD3199, AZD5069 (CXCR2), AZD5423

(inhaled SEGRA), AZD8683 (muscarinic antagonist), BCT197, BI-137882, BIO-11006, Dulera mometasone/formoterol, EP-101 (LAMA), EP-102 (LAMA/LABA), EPI-12323, formoterol/fluticasone fixed-dose combination (inhalation), GSK256066 (inhaled PDE4 inhibitor), GSK573719 (muscarinic acetylcholine antagonist), GSK573719/vilanterol (muscarinic acetylcholine antagonist/long-acting beta2 agonist), GSK610677 (inhaled p38 kinase inhibitor), GSK961081 (muscarinic antagonist/beta2 agonist), GSK1325756 (chemokine receptorantagonist-2), GSK2245840

(SIRT1 activator), Ilaris canakinumab, LAS 100977 (LABA), levosalbutamol/ipratropiuminhalation solution, losmapimod (oral p38 kinase inhibitor), MEDI-2338 (anti-IL-mAb), MEDI-8968 (anti-IL-1R), MK-7123 (navarixin), MN-166 (ibudilast), MN-221 (bedoradrine), NVA237

(glycopyrrolate inhalation), O-desulfated heparin intravenous, olodaterol, olodaterol/tiotropium bromide, paclitaxel-loaded stent, PF-03715455, PH-797804, Prochymal remestemcel-L, PT001 (glycopyrrolate inhalationaerosol), PT003 (glycopyrrolate/formoterol inhalation aerosol), PT005 (formoterol inhalation aerosol), PUR118, QMF149 (indacaterol/mometasone), QVA149 (glycopyrrolate/indacaterol inhalation), Relovair vilanterol/fluticasone furoate, RV568, TD-4208(LAMA), tetomilast, vilanterol (long-acting beta2 agonist), Veldona interferon-alpha, and a combination thereof.

The inhaler of the present invention may be adapted for topical administration or for systemic absorption of drugs delivered for the local treatment of respiratory disease. The inhaler is further efficient and reproducible systemic delivery is lung deposition.

The inhaler of the present invention may be used with therapeutic agents that are antiasthmatics, including bronchodilators and anti-inflammatories, particularly of steroid type, having a local therapeutic action in the lungs and/or a systemic therapeutic action after absorption in tree blood.

The inhaler of the present invention are also suitable for dispensing any medicaments which may be administered in aerosol formulations and useful in inhalation therapy e.g.; anti-allergics, e.g. cromoglycate (e.g. as the sodium salt), ketotifen or nedocromil (e.g. as sodium (salt); anti-inflammatory steroids, e.g. beclomethasone (e.g. as dipropionate), fluticasone (e.g. as propionate), flunisolide, budesonide, rofleponide, mometasone (e.g as furoate), ciclesonide, triamcinolone acetonide; anticholinergics, e.g. ipratropium (e.g. as bromide), tiotropium, atropine or oxitropium and salts thereof. It will be clear to a person skilled in the art that, where appropriate, the medicaments may be used in the form of salts, (e.g. as alkali metal or amine salts or as acid addition salts) or as esters (e.g. lower alkyl esters) or as solvates (e.g. hydrates) to optimize the activity and or stability of the medicament and/or to minimise the solubility of the medicament in the propellant. Medicament may be used in the form of racemate or in the form of a pure isomer e.g. R-salmeterol or S-salmeterol.

In another embodiment of the present invention, the LG is released to LG-containing volume using an LG-release valve means 2 which may further control the LG-pressure delivered to the inhaler. The LG source is provided as a gaseous propellant having vapor pressure.

In another embodiment of the present invention, the air pressure-operated inhaler of the present invention is provided with at least two configurations. One configuration is before activating the LG source therefore the air actuator is in a resting position. The second configuration is when activating the LG valve and releasing LG for compressing the air actuator for releasing air flow from the inhaler air outlet.

In another embodiment of the present invention, the inhaler can be used as a dispensing system for creating an aerosol mist of liquid particles.

In another embodiment of the present invention, the inhaler is suitable for infants, small children and elderly patients or patients with nerve or muscle weakness.

In another embodiment of the present invention, the inhaler is a portable device and is effective for short and long treatment. Furthermore, the inhaler provides an improved lung deposition. The inhaler is constructed such that the actuator allows the delivery of a sufficient amount of a compressed air and directs the compressed air flow in such manner toward the air outlet such that an entire mass of a latter is released from the inhaler.

In another embodiment of the present invention, the LG is preferably Liquefied petroleum gas, also known as LPG, GPL, LP Gas, liquid petroleum gas or simply propane or butane. The LPG is a flammable mixture of hydrocarbon gases used as an aerosol propellant.

In another embodiment of the present invention, the inhaler the present invention may comprise a compressed or pressurized gas.

The LG is further selected from the group consisting of: 1,1,1,2-tetrafluoroethane (HFA 134a) or 1,1,1,2,3,3,3-heptafluoropropane (HFA 227) or a mixture thereof. In alternative propellants such as carbon dioxide or other which are gaseous at room temperature and standard atmospheric pressure may be used.

The inhaler of the present invention may further adapted for releasing a therapeutic agent or nontherapeutic agent such as fragrances, paints, stains, dyes, inks, lacquers, urethanes or lubricants.

Figure 2:
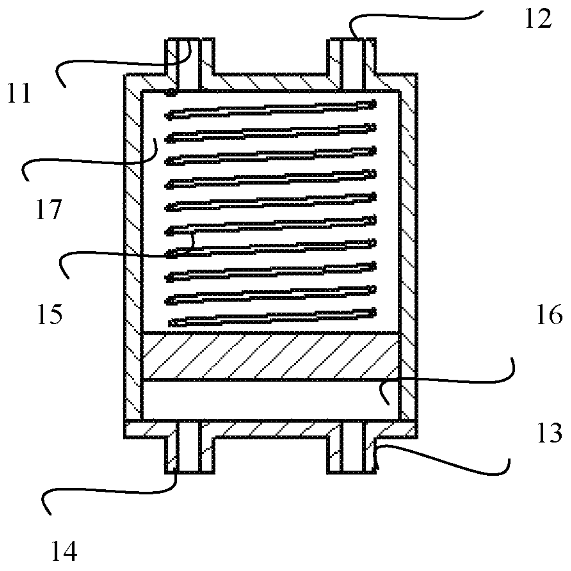
FIG. 2 presents a schematic view of the metered dose inhaler of the present invention comprising a piston pump as an actuator.

Reference is now made to FIGS. 2 and 3 which illustrate a schematic view of a metered dose inhaler, comprising: an air actuator comprising at least one inlet of liquefied gas (LG), at least one air outlet, at least one first LG-expanding volume and at least one second air-containing volume. The first and second volumes are effectively separated by means of an LG-blocking member. The LG source in the present invention may be a separated LG container. The container is in a fluid connection with LG-expanding volume via at least one LG inlet.

The air actuator is adapted to facilitated a metered dose airflow by allowing the expansion of the LG in the at least one LG-expanding volume from its condensed liquid phase to its expanded gas phase. Furthermore the expansion of the LG facilitates the compression of the air within the at least one air-containing volume, such that a metered dose LG-free air flow is inhalable via the at least one air outlet The actuator means presented in FIG. 2 is a piston pump or plunger 15 which acts as a recoil spring-like. The piston is an air-compressing piston which further configured as a barrier between the LG-expanding volume 16 and the air-containing volume 17. The compressed LG applies a force upon the piston 15 toward the air-containing volume 17 to release air flow.

Furthermore air may be compressed to apply a force upon the piston toward the LG volume to disposed LG flow. The piston allows the LG and the air to remain separately at all times such that the compressed air is released at a predetermined pressure via the air outlet 12. The piston 15 is coupled to the air-containing volume 17 such that that the piston is biased toward air-containing volume. The piston further controls the flow rate of the pressurized air.

The inhaler of the present invention comprises at least one air outlet 12 for releasing compressed air and air inlet 11 for air entrance to the air-containing volume 17. When air is inserted to the air-containing volume the piston 15 is in its unpressurized configuration meaning inactivating position. Furthermore, when air is released from the air-containing volume 17, the piston is in its pressurized configuration, meaning activating position.

The inhaler of the present invention further comprises at least one LG inlet 14 for LG entrance to the LG-volume portion 16 within the inhaler for compressing the piston to its pressurized configuration. The inhaler may further comprise an LG outlet 13 for LG exit when the piston is in its unpressurised configuration and, in parallel air is inserted into the inhaler through the air inlet. The opening and closing of the LG inlet, air inlet and LG and air outlets are controlled by the movement of the actuator.

In another embodiment of the present invention, the LG container comprises propane, butane and a mixture thereof.

The inhaler of the present invention is configured for spraying at least one dose selected from a group consisting of a gas material, fine particles, liquid material, powder form and a combination thereof.

In another embodiment of the present invention, the inhaler may be a portable device and/or a handheld device.

Figure 3A:
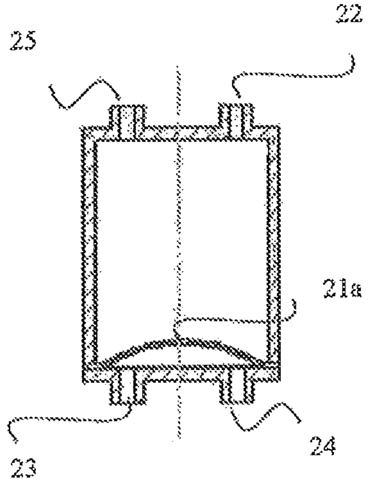
FIGS. 3A-B present a schematic view of the metered dose inhaler of the present invention comprising an inflatable membrane as an actuator.
Figure 3B:
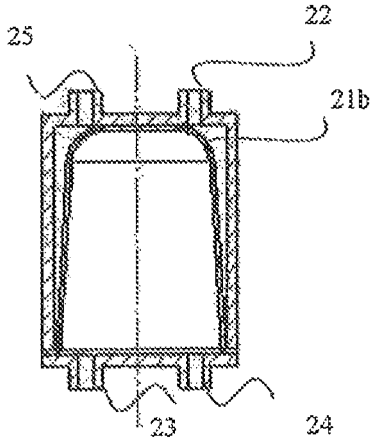

Reference is now made to FIGS. 3*a-b* which illustrate a schematic view of the metered dose inhaler container of the present invention, comprising: an air actuator such as a membrane 21 comprising at least one inlet of liquefied gas (LG) 23, at least one air outlet 22, at least one first LG-expanding volume and at least one second air-containing volume. The first and second volumes are effectively separated by means of an LG-blocking member.

The inhaler further comprises a container with LG source. The container is in a fluid connection with LG-expanding volume via at least one LG inlet. The inhaler may further comprise an LG outlet 24 for LG exit when the membrane is in its deflated configuration and, in parallel air is inserted into the inhaler through the air inlet 25.

The air actuator is facilitating a metered dose airflow by allowing the expansion of the LG in the at least one LG-expanding volume from its condensed liquid phase to its expanded gas phase. Furthermore the expansion of the LG facilitates the compression of the air within the at least one air-containing volume, such that a metered dose LG-free air flow is inhalable via the at least one air outlet The air actuator is an inflatable membrane 20, adapted to release a flow of compressed air through the air outlet at such time as a predetermined LG pressure has been reached in the volume adapted to contain LG.

The membrane is provided in two configurations, inflated configuration 21*b* and deflated configuration 21*a*. The inflatable membrane is further configured to provide a barrier between air-containing volume and the LG volume portion. The inflated membrane further allows the LG and the air to remain separately at all times such that the compressed air is released at a predetermined pressure. The membrane is inflated by activated LG pressure in order to compress air via the air outlet 22. The membrane is an expandable flexible elastic member.

In another embodiment of the present invention, the membrane is configured as a diaphragm-like shape or condom-like shape, composed of an elastic resilient material, whereby the slit of the membrane will open at a given excess pressure in the compression air containing volume.

FIG. 3*a* further illustrate the inhaler in a deflated configuration meaning unpressurized configuration. FIG. 43*b* illustrated the inflatable configuration meaning pressurized configuration.

Figure 4:
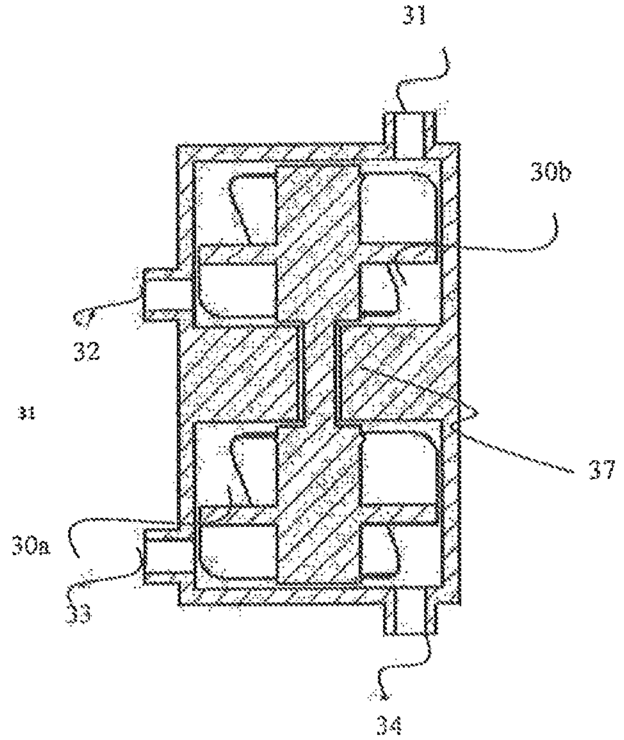
FIGS. 4 and 5 presents a schematic view of the metered dose inhaler of the present invention comprising turbine-compressor means as an actuator.
Figure 5:
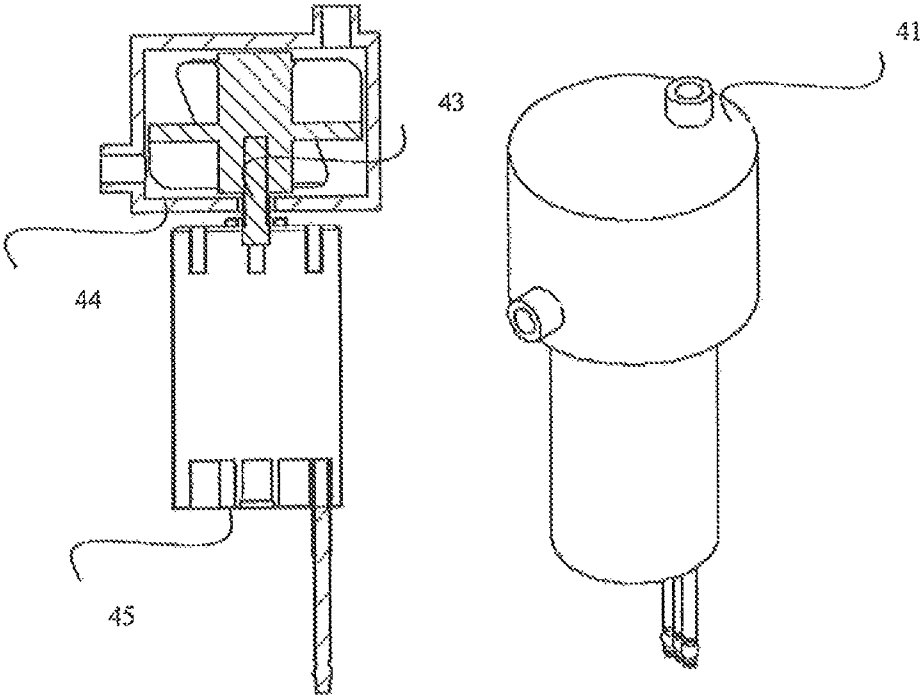

Reference is now made to FIGS. 4 and 5 which illustrate a schematic view of the metered dose inhaler container of the present invention, comprising: an air actuator 30*a-b* comprising at least one inlet of liquefied gas (LG), at least one air outlet 31, at least one first LG-expanding volume and at least one second air-containing volume.

In another embodiment of the present invention, the first and second volumes may be effectively separated by means of an LG-blocking member.

The inhaler further comprises a container with LG. The container is in a fluid connection with LG-expanding volume via at least one LG inlet 33.

The air actuator is facilitating a metered dose airflow by allowing the expansion of the LG in the at least one LG-expanding volume from its condensed liquid phase to its expanded gas phase. Furthermore the expansion of the LG facilitates the compression of the air within the at least one air-containing volume, such that a metered dose LG-free air flow is inhalable via the at least one air outlet The air actuator is a turbine-compressor, impeller or a rotor-compressor 30*a-b*, adapted to release a flow of compressed air through the air outlet at such time as a predetermined LG pressure has been reached in the LG-expanding volume.

The rotor is operated by pressurized LG in order to compress air flow via the air outlet 31. As FIG. 4 illustrates, the inhaler comprising two rotors 30*a* and 30*b*, which are fixedly connected to an axle 37 such that the angular velocity of the axle is such as the angular velocity of the two rotors. The inhaler may further comprise an LG outlet 34 for LG exit when the second rotor 30*b* is in its spinning configuration and, in parallel air is inserted into the inhaler through the air inlet 32.

In another embodiment of the present invention the inhaler may comprise at least one energy source which further may replace the LG source for compressing the actuator.

The energy source is selected from the group consisting of: electric motor, electric linear actuator, electromagnetic solenoid based actuator, spring operated mechanism, hydraulic pump, compressed gas—CG, flywheel, heat engine of sorts (such as, steam engine, carnot machines, stirling cycle) and a combination thereof. FIG. 5 further illustrates an impeller housing 41 comprising an energy source such as a motor or engine 45 fixedly connected to a rotor actuator 44 via an axle 43 such that the angular velocity of the axle is such as the angular velocity of the rotor and the motor. In another embodiment of the present invention, the turbine acts as a rotary mechanical device that extracts energy from a gas flow and converts it into useful work energy therefore to release air from the inhaler. The turbine illustrated is a turbo-machine having at least one moving part, a rotor assembly, which is a shaft or drum with blades attached. The moving gas or fluid acts on the blades so that they move and impart rotational energy to the rotor. A working gas or fluid contains potential energy and kinetic energy. The gas or fluid may be compressible or incompressible. Impulse turbines change the direction of flow of a high velocity fluid or gas jet. The resulting impulse spins the turbine and leaves the fluid flow with diminished kinetic energy. There is no pressure change of the fluid or gas in the turbine blades, as in the case of a steam or gas turbine, all the pressure drop takes place in the stationary blades (the nozzles). Before reaching the turbine, the fluid's pressure head is changed to velocity head by accelerating the fluid with a nozzle. Impulse turbines do not require a pressure casement around the rotor since the fluid jet is created by the nozzle prior to reaching the blading on the rotor. Reaction turbines develop torque by reacting to the gas or fluid's pressure or mass. The pressure of the gas or fluid changes as it passes through the turbine rotor blades. A pressure casement is needed to contain the working fluid as it acts on the turbine stage(s) or the turbine must be fully immersed in the gas or fluid flow. The casing contains and directs the working fluid and, for water turbines, maintains the suction imparted by the draft tube. For compressible working fluids, multiple turbine stages mat be used to harness the expanding gas efficiently.

Figure 6:
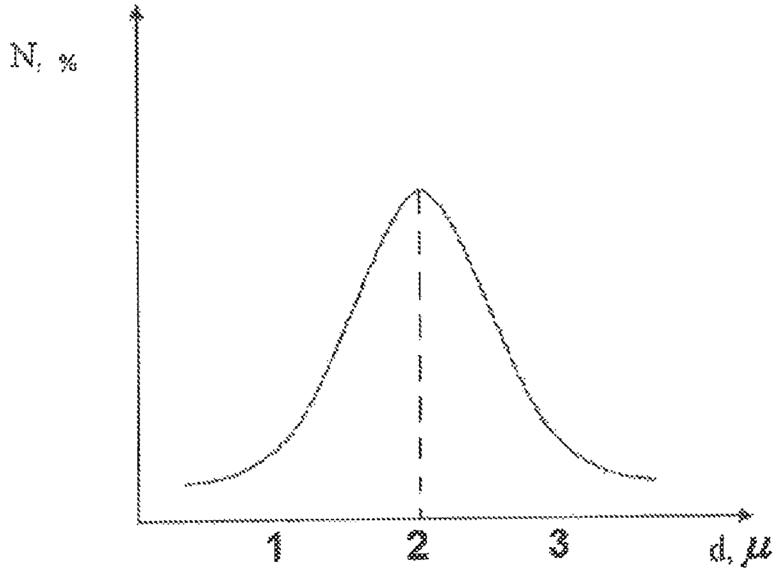
FIG. 6 presents a graph of the droplets size vs. the droplets percentage amount of the metered dose inhaler of the present invention.

Reference is now made to FIG. 6 which illustrates a Gaussian curve of the droplets diameter of a medication dispersed from the inhaler of the present invention vs. the particles percentage amount. As illustrated, the inhaler may provide more that 50% droplets from the medication droplets population having a 2 mμ diameter. Furthermore, the inhaler may further provide more than 75% droplets from the medication droplets population having a 3 mμ diameter.

Figure 7A:
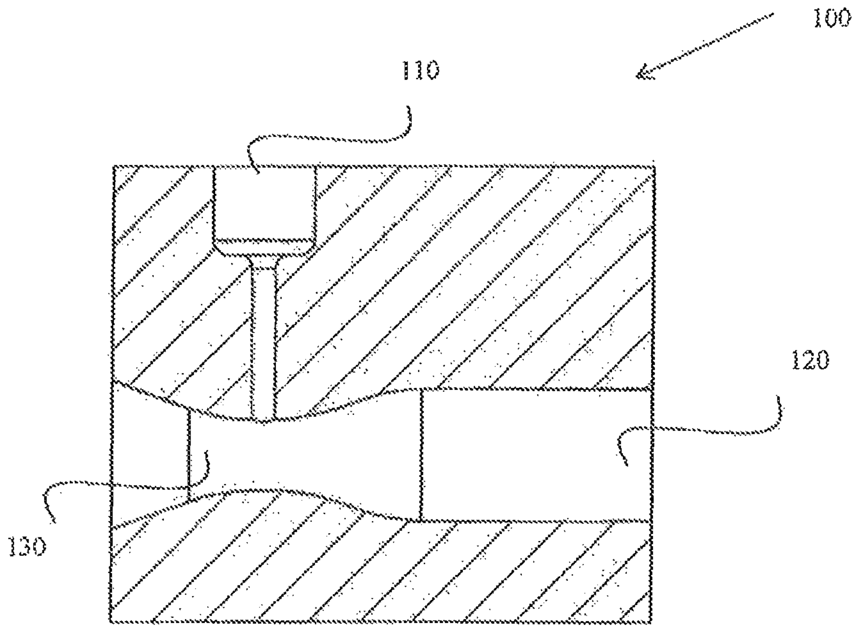
FIG. 7 presents a cross section view of the venturi nozzle system of the metered dose inhaler of the present invention.
Figure 7B:
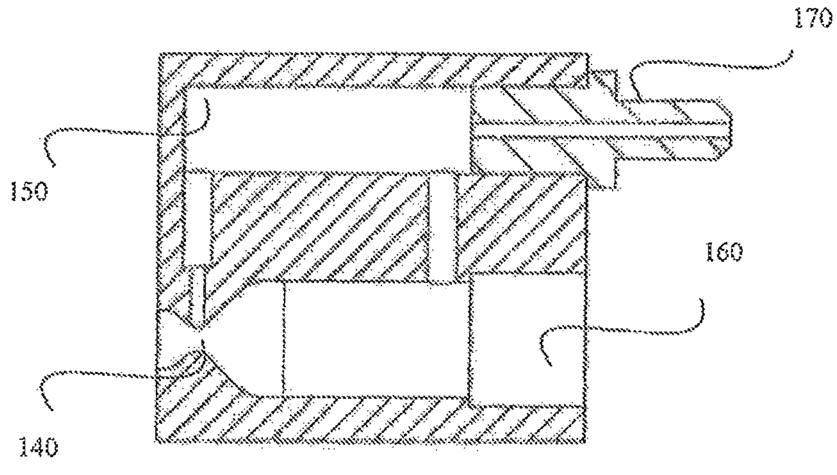

Reference is now made to FIGS. 7*a-b* which further illustrate the inhaler of the present invention comprising a venturi nozzle system 100 having an air inlet 120, a medication inlet 110 and a medication-air mixture outlet 130. The venturi nozzle system is designated for the medication rate of flow comparing to the air rate of flow and further for decrease the medication droplet size or medication particle size. The medication particle size dispersed from the inhaler of the present invention is proportional to the air velocity due to the shear forces and surface tension balance on each droplet.

The nozzles system 100 of the present invention is configured to dispense an effective measure of a medicament in the form of a mist. The system comprises an inhaler comprising an air actuator comprising at least one inlet of liquefied gas (LG), at least one air outlet, at least one first LG-expending volume and at least one second air-containing volume, the first and second volumes are effectively separated by means of an LG-blocking member, a container with a LG source. The container is in a fluid connection with the LG-expending volume via at least one LG inlet, valve means in communication with the air actuator and at least two nozzles in fluid communication with the inhaler's air outlet.

FIG. 7*a* further illustrates a classic venturi nozzles system 100 comprising an air inlet 120, a medication inlet 110 and a medication-air mixture outlet 130. The venturi nozzles system is designated for the medication rate of flow comparing to the air rate of flow and further for decrease the medication droplet size or medication particle size. The medication particle size dispersed from the inhaler of the present invention is proportional to the air velocity due to the shear forces and surface tension balance on each droplet.

FIG. 7*b* further illustrates a cross section of the inhaler of the present invention comprising venturi nozzles in a predefined arrangement. The venturi nozzle is based upon a push and pulls mechanism. The inhaler comprises an air inlet 160 for delivering air flow, a medication inlet 170, a medication reservoir 150 and an air-medication mixture outlet 140 for delivering the fluid or medication droplets. The air inlet diameter is configured to provide a pressure difference such that the downstream pressure may further empty the inner cavity of the liquid reservoir and prevent unnecessary residuals resulting from low pressure or any fluid adherent within the inhaler. The venturi nozzle, low pressure mixing chamber and the air-containing volume are configured such that at standard temperature and pressure (STP) a differential pressure results in no medication that is drawn upward through the primary suction line for nebulization and discharged through the inhaler outlet until a negative inspiratory pressure is created from inhalation by the subject. Furthermore, the venturi nozzle may be horizontally oriented when in use.

It is another embodiment of the present invention, at least one nozzle is configured with a diameter of about 0.2 mm to about 0.9 mm to provide a droplets distribution of more than 70% of a medication.

It is another embodiment of the present invention, at least one nozzle is with a diameter of about 0.5 mm to disperse a droplets size is in a range of about 2μ to about 3μ.

Preferably, the overall cross sectional area of the nozzle outlets is 25 to 500 square micrometers.

As FIG. 7*b* demonstrates, the air within the air inlet flow via constricted section with a reduced diameter, the reduction in diameter causes an increase in the fluid flow speed thus the velocity of the fluid increases as the cross sectional area decreases, with the static pressure correspondingly decreasing resulting a fluid suction. Thereby, an increase in the speed of the fluid occurs simultaneously with a decrease in pressure or a decrease in the fluid's potential energy (e.g Venturi effect). Furthermore, when the fluid such as a medication, flows through the nozzle tube that narrows to a smaller diameter, the partial restriction causes a higher pressure at the inlet than that at the narrow end. This pressure difference causes the fluid to accelerate toward the low pressure narrow section, in which it thus maintains a higher speed. The direct relationship between pressure difference and fluid speeds may further allow to determine the volumetric flow rate.

In another embodiment of the present invention, in order to provide a negative pressure, thus sucking in all of the fluid, the liquid reservoir is further connected to an additional narrow tube which further configured to provide additional pressure from the back side of the liquid reservoir. The additional pressure enables and accelerates the reservoir emptying from the remained liquid droplets.

The venturi nozzles system is designated for the medication rate of flow comparing to the air rate of flow and further for decreasing the medication droplet size or medication particle size.

The medication particle size dispersed from the nozzles system of the present invention is proportional to the air velocity due to the shear forces and surface tension balance on each droplet.

The formulation below demonstrates the calculation of flow rate using and orifice and/or venturi nozzle for incompressible flow, based on the Bernoulli principle:

$$\frac{p_1}{\rho}+\frac{v_1^2}{2}+g\ z_1=\frac{p_2}{\rho}+\frac{v_2^2}{2}+g\ z_2+\frac{\Delta p_{1-2}}{\rho}$$

where is:

p—pressure

ρ—density

V—velocity g—gravitational constant (9.81 m/s2)

z—geodetic height

Assumption that pressure lost is negligible (pressure drop is obvious and included with coefficient of discharge which is introduced below):

$$\Delta\rho_{1\text{-}2}=0$$

and:

$$gz_1=gz_2$$

and if velocities substituted with flow rate:

$$V_1=\frac{4Q}{\pi D_1^2}\ V_2=\frac{4Q}{\pi D_2^2}$$

where is:

Q—volumetric flow rate

D—diameter

Pressure drop through the orifice resulting from the increase of velocity which may be calculated as follows:

$$\frac{p_1-p_2}{\rho}=\frac{1}{2}\left(\frac{16Q^2}{\pi^2 D_2^4}-\frac{16Q^2}{\pi^2 D_1^4}\right)$$

or:

$$\frac{2(p_1-p_2)}{\rho}=\frac{16Q^2}{\pi^2}\left(\frac{1}{D_2^4}-\frac{1}{D_1^4}\right)$$

Expressing flow rate from the previous equation leads to:

$$Q=\sqrt{\frac{1}{1-\left(\frac{D_2}{D_1}\right)^4}}\frac{\pi D_2^2}{4}\sqrt{\frac{2(p_1-p_2)}{\rho}}$$

Additional values are calculated using following equations:

Mass Flow:

$$G=\rho Q$$

Velocities:

$$V_1=\frac{4Q}{\pi D_1^2}\ V_2=\frac{4Q}{\pi D_2^2}$$

Figure 8:
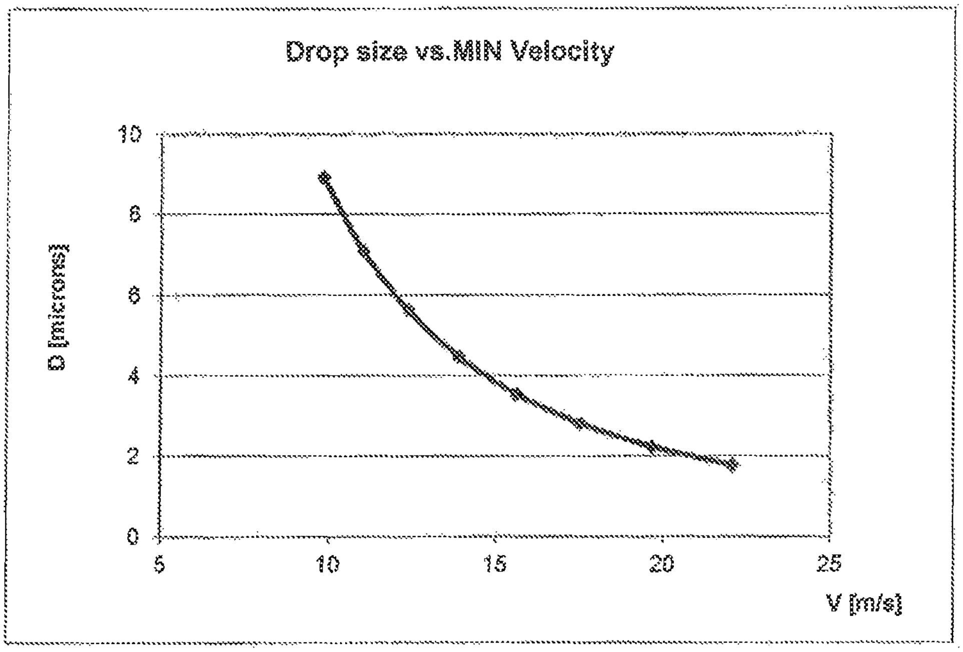
FIG. 8 presents a graph of the droplets size vs. the droplets velocity of the metered dose inhaler of the present invention.

Reference is now made to FIG. 8 which illustrates a graph of the droplets diameter vs. the velocity of the medication dispersed from the metered dose inhaler of the present invention.

The droplets size is determined according to relevant ration of at least one inlet and outlet in the inhaler. Thereby, the droplets size is determined according the diameter of the air inlet, the medication inlet and the nozzle outlet. As FIG. 8 illustrates, a droplets diameter is exponentially decrease at a rate proportional to the velocity, thereby the droplets diameter consequently follow exponential decay. For example, droplets having a diameter of about 4μ may be obtained from the inhaler in a velocity of about 15 m/s. Droplets having a diameter of about 2μ may be obtained from the inhaler in a velocity of about 20 m/s.

Figure 9:
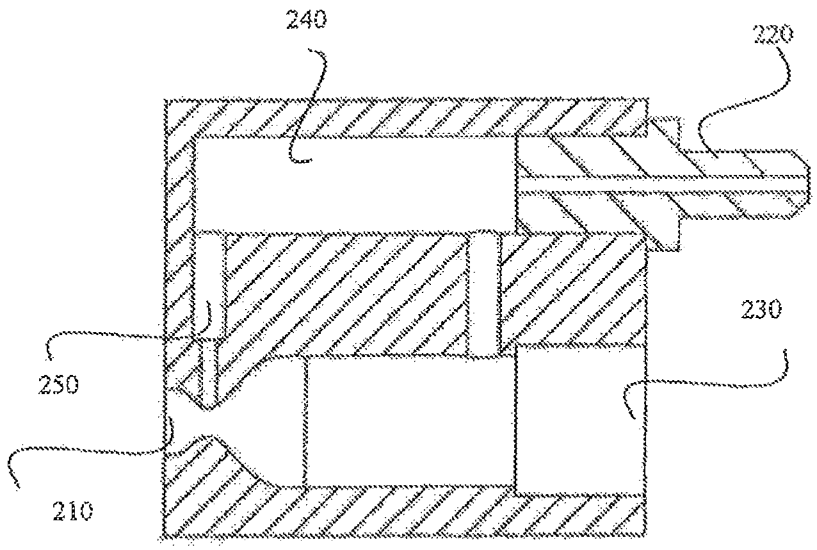
FIG. 9 presents a cross section of the metered dose inhaler of the present invention comprising a venturi system for dispersing medication; and, FIGS. 10-11 present graphs of a medication droplets distribution of the inhaler comprising a dual nozzle, of the present invention.

Reference is now made to FIG. 9 which illustrates a cross section of the metered dose inhaler of the present invention comprising a venturi nozzle which is a based upon a push and pull mechanism. The meter dose inhaler comprises an air inlet 230 for delivering air flow, a medication inlet 220, a medication reservoir 240 and an air-medication mixture outlet 210 for delivering the fluid or medication droplets. The air inlet diameter is configured to provide a pressure difference such that the downstream pressure may further empty the inner cavity of the liquid reservoir and prevent unnecessary residuals resulting from low pressure or any fluid adherent within the inhaler. As FIG. 9 demonstrates, the air within the air inlet flow via constricted section with a reduced diameter, the reduction in diameter will cause an increase in the fluid flow speed thus the velocity of the fluid increases as the cross sectional area decreases, with the static pressure correspondingly decreasing resulting a fluid suction. Thereby, an increase in the speed of the fluid occurs simultaneously with a decrease in pressure or a decrease in the fluid's potential energy (e.g Venturi effect). Furthermore, when the fluid such as a medication, flows through the tube that narrows to a smaller diameter, the partial restriction causes a higher pressure at the inlet than that at the narrow end. This pressure difference causes the fluid to accelerate toward the low pressure narrow section, in which it thus maintains a higher speed. The direct relationship between pressure difference and fluid speeds may further allow to determine the volumetric flow rate.

In another embodiment of the present invention, in order to provide a negative pressure, thus sucking in all of the fluid. The liquid reservoir is further connected to an additional narrow tube 250 which further configured to provide additional pressure from the back side of the liquid reservoir. The additional pressure enables and accelerates the reservoir emptying from the remained liquid droplets.

In another embodiment of the present invention, the metered dose inhaler meets and compliance with FDA regulations.

Tale 2 below presents the advantages of the inhaler of the present invention, compared to variety devices present in the market:

| Category | MDI (Metered-dose inhalers) | DPI (Dry powder inhalers) | Respimat ™ | Inhealer ™ | Inhealer ™'s Advantages |
|---|---|---|---|---|---|
| Particle average size | ~4 μm | ~5 μm | Under 5.8 μm | Adjustable between one or more of the following rangers: 0.5-7.5 μm, or 0.5-2.5 μm, or 2.5-5.0 μm or 5.0-7.5 μm | Improved alveolar deposition & improved surface/volume ratio, thereby increase loading and kinetics per dosage |
| Duration of inhaled cloud/mist | 0.15-0.36 sec | Under 0.2 sec | 1.5 sec | 0.5-2.5 sec | Improved absorption |
| Propulsion gas | CFC/HFA (chlorofluoro carbons/hydrofluorocarbons) | None - breath actuated | None-spring driven | None | Lower costs |
| Disadvantages | Dependence on propulsion gas. | Dependence on patient's respiration. | Dependence on specialized nozzle-clogging. | None | No propulsion gas, Not breath dependent, use of common reliable nozzle. |

Figure 10:
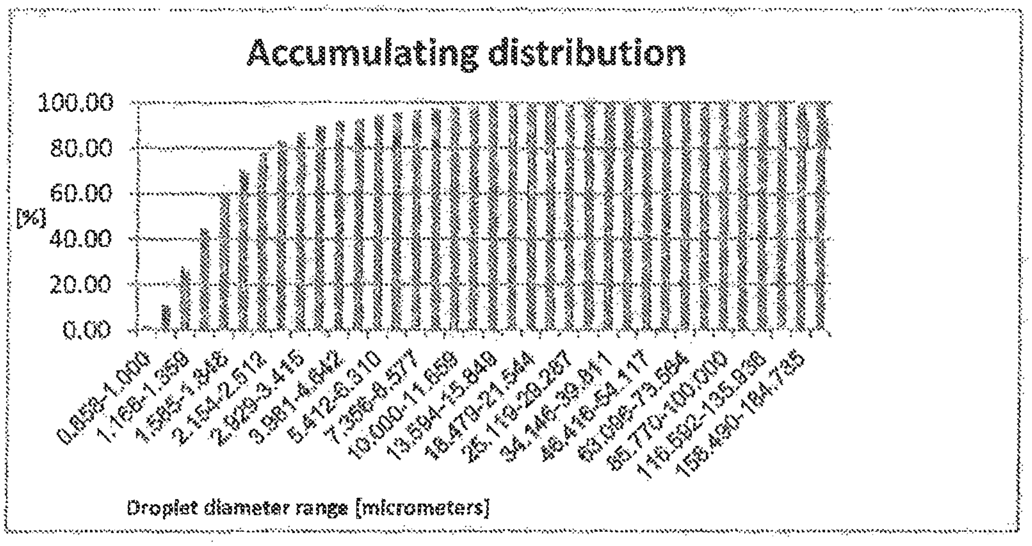
Figure 11:
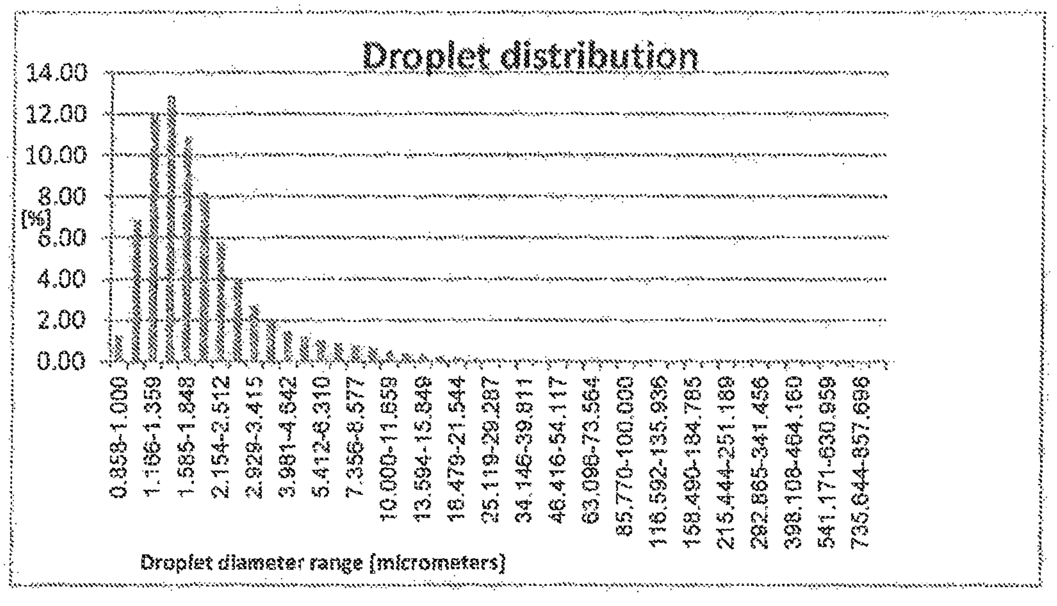

Reference is now made to FIGS. 10 to 11 which illustrate graphs of droplets distribution and droplets accumulating distribution which determine the quality of the mist sprayed out of the present invention's custom designed nozzles system.

FIG. 10 further demonstrates a Gaussian curve of the droplets diameter of a medication dispersed from the inhaler comprising the nozzles system of the present invention vs. the particles percentage amount. As illustrated, the inhaler may provide more that 50% droplets from the medication droplets population having a 2 mμ diameter. Furthermore, the inhaler may further provide more than 75% droplets from the medication droplets population having a 3 mμ diameter. The graph is characterized by a bell-shaped curve of the diffusion of medication particles which further illustrates that an optimal absorption percentage of medication can be achieved in droplets size in the range of about 0.8μ to about 6μ.

The inhaler was further tested using the MALVERN Spray tech particle sizing analyzer for determining the droplets diameter and duration vs. the medication dispersed dose.

Table 3 below demonstrates the particle size and distribution when using the inhaler of the present invention. The inhaler of the present invention is with ability to generate a mist that consists of 80% droplets smaller than 3 microns and 90% droplets smaller than 5 microns.

TABLE 3

| | NOZZLE EXP | | |
|---|---|---|---|
| CRITERIA | Peak particle size [μ] | Accumulated distribuition >75% range [μ] | Accumulated distribuition >80% range [μ] |
| 1_3.5b_27 mms_C | ~1.8 | 1.848-2.154 | 2.154-2.512 |
| 1_3.5b_27 mms_D | ~2.0 | 1.848-2.154 | 2.154-2.512 |
| Summary 3.5 bar | ~2.0 | 1.848-2.154 | 2.154-2.512 |
| 1_4b_27 mms_3 | ~1.5 | 2.154-2.512 | 2.512-2.929 |
| 1_4b_27 mms_4 | ~1.4 | 2.154-2.512 | 2.512-2.929 |
| Summary 4 bar | ~1.5 | 2.154-2.512 | 2.512-2.929 |
| DBL_3.2B_1 | ~4.3 | 7.356-8.577 | 7.356-8.577 |

The present invention further provides a inhaler for improving medicament's alveolar deposition is with a medication lunching velocity of about 40 μL/s, air velocity of about 100 cc/s, whilst the minimum diameter of the tube of the venturi system is of about 0.95 mm and the minimum diameter of the medication inlet is of about 0.38 mm. This results an air-medication mixture having a velocity of about 20 m/s. The inhaler further provides droplets with an average diameter of about 2.4μ.

In another embodiment of the present invention, the inhaler may further be adapted for systemic administration of active compounds and drug compositions (e.g via a route of administration of medication nutrition or other substance into the circulatory system so that the entire respiratory system is affected), therefore, adapting the respiratory system as a port of entry for systemic distribution and/or absorption of drugs (e.g. insulin) via enteral administration.

The present invention further provides a method of dispersing a dose from a metered dose inhaler, comprising steps of: providing a metered dose inhaler with an air actuator, providing at least one inlet of liquefied gas (LG), at least one air outlet, at least one first LG-expanding volume and at least one second air-containing volume, providing the first and second volumes separated by means of an LG-blocking member; a container with an LG; providing the container in a fluid connection with the LG-expanding volume via the at least one LG inlet; and then releasing the LG directly to the actuator; wherein the method of releasing the LG directly to the actuator further comprises steps of facilitating metered dose airflow by an air actuator thereby allowing the expansion of the LG in the LG-expanding volume from its condensed liquid phase to its expanded gas phase; and further wherein the method additionally comprising steps of facilitating the compression of the air within the air-containing volume by the expansion of the LG, such that a metered dose LG-free air flow is inhaled via the air outlet.

In another embodiment of the present invention, the method additionally comprising step of selecting the air actuator from a group consisting of a piston pump, a rotor, a turbine, an inflatable membrane and a combination thereof.

In another embodiment of the present invention, the method additionally comprising steps of configuring the membrane as a diaphragm or condom.

In another embodiment of the present invention, the method additionally comprising step of providing a mist nozzle in a fluid connection with the inhaler.

In another embodiment of the present invention, the method additionally comprising step of selecting the LG from a group consisting of liquefied petroleum gas (LPG), propane, butane and a mixture thereof.

In another embodiment of the present invention, the method additionally comprising step of selecting a medicament from a group consisting of solid form, gas form, liquid form and a mixture thereof.

In another embodiment of the present invention, the method additionally comprising step of configuring the inhaler for spraying at least one dose form selected from the group consisting of a gas material, a flow material, fine particles, a liquid material, a powder material and a mixture thereof.

In another embodiment of the present invention, the method additionally comprising step of providing the inhaler as a portable and handheld device.

The present invention further provides a method of treating respiration disorders in a patient which comprises use by the patient of a metered dose inhaler as described in the present invention.

The present invention further provides a device operative in a method of dispersing a dose, comprising steps of: providing a metered dose inhaler with an air actuator comprising at least one inlet of liquefied gas (LG), at least one air outlet, at least one first LG-expanding volume and at least one second air-containing volume, the first and second volumes are effectively separated by means of an LG-blocking member; providing a container with an LG source; the container is in a fluid connection with the LG-expanding volume via the at least one LG inlet; releasing the LG directly to the actuator; wherein the step of releasing the LG directly to the actuator is followed by an additional step of facilitating a metered dose airflow by the air actuator, thereby allowing the expansion of the LG in the LG-expanding volume from its condensed liquid phase to its expanded gas phase, and further wherein the step is followed by an additional step of facilitating the compression of the air within the air-containing volume by the expansion of the LG, such that a metered dose LG-free air flow is inhaled via the air outlet.

The present invention further provides a metered dose inhaler for improving medicament's alveolar deposition comprising:

at least one inlet of liquefied gas (LG) communicating with at least one first volume for LG-expansion;

at least one second volume for containing a medicament, the second volume in in fluid connection with at least one medicament outlet;

an air actuator configured for moving air and the medicament towards patient's respiratory tract; and a container with a liquefied LG source, the container is in fluid connection with the first volume, where the LG is allowed to gasify, via the at least one LG inlet;

The air actuator comprises an LG-blocking member separating the first volume where LG is in liquid phase and the second volume where the LG is in it gas phase; and wherein the LG-blocking member moveable towards the medicament outlet by means of a pressure exerted by the LG-phase transition, thereby emitting effective measure of the medicament.

In another embodiment of the present invention, the metered dose inhaler for improving medicament's alveolar deposition is with a medication lunching velocity of about 40 μL/s, air velocity of about 100 cc/s, whilst the minimum diameter of the tube of the venturi system is of about 0.95 mm and the minimum diameter of the medication inlet is of about 0.38 mm. This results an air-medication mixture having a velocity of about 20 m/s. The metered dose inhaler further provides droplets with an average diameter of about 2.4μ.

The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A metered dose inhaler for use in dispensing a dose of a medicament, the inhaler comprising:

an air actuator comprising:

at least one first liquefied gas (LG) expanding volume in a fluid connection with an LG source container via at least one LG inlet, the inhaler further comprising at least one LG outlet wherein said at least one air inlet is separate and distinct from said at least one air outlet;

at least one second air-containing volume fluidly connected to at least one air outlet and to at least one air inlet enabling insertion of air into the at least one second air-containing volume; and an inflatable membrane configured for separating said at least one first LG-expanding volume and said at least one second air-containing volume such that said LG and said air remain separate at all times, said inflatable membrane being adapted to release a flow of compressed air through said at least one air outlet when a predetermined LG pressure has been reached within said at least one first LG-expanding volume; and a nozzle system having at least one nozzle including a nozzle air inlet in fluid communication with said at least one air outlet, a medication inlet in communication with a medication container, a nozzle air-mixture outlet, and a constricted section with a reduced cross-section located between said nozzle air inlet and said nozzle air-mixture outlet;

wherein, when the inflatable membrane is deflated, said air enters into the at least one second air-containing volume through the at least one air inlet and, when LG enters the at least one first LG-expanding volume, the inflatable membrane is inflated, compressing said air in the at least one second air-containing volume, thereby releasing said flow of compressed air through said at least one air outlet; and wherein dimensions of said nozzle system are selected to provide a steady and high velocity of air flow at the nozzle air-mixture outlet, and to provide a particle size of medicament droplets being proportional to the steady and high velocity of the air flow.

2. The inhaler according to claim 1, wherein said nozzle air-mixture outlet is configured with an orifice having one of the following configurations: a diameter of about 0.2 mm to about 0.9 mm, or configured to emit an effective amount of the medicament droplets having an average particle size equal to or less than 5.0 μm.

3. The inhaler according to claim 1, wherein said LG is selected from the following: liquefied petroleum gas (LPG), propane, butane and a combination thereof.

4. The inhaler according to claim 1, wherein said medication container is configured for containing medicament in a form selected from solid form, gas form, liquid form and a combination thereof.

5. The inhaler according to claim 1, wherein said inhaler is portable and handheld.

6. The inhaler according to claim 1, further comprising an LG directing valve configured and operable for activating the LG source container, allowing expansion of said LG in said at least one first LG-expanding volume from its condensed liquid phase to its expanded gas phase, thereby providing that said at least one first LG-expanding volume contains LG compressed between about 20 and about 200 psig; said compressed LG applying a force upon said inflatable membrane for compression of said air within said at least one second air-containing volume having predetermined pressure between 3 and about 10 psig, thereby causing release of airflow via said at least one air outlet and providing a metered dose of said medicament droplets having an average size in the range of about 1 μm to about 5 μm inhalable by a user.

7. The inhaler according to claim 1, further comprising a medicament metering valve configured to control a release of a specific amount of medication from the medication container to the nozzle system.

8. The inhaler according to claim 1, wherein said nozzle system further comprises an additional air outlet connected to a backside of the medication container in order to provide additional pressure from the backside of the medication container, thereby accelerating emptying of the medicament droplets from the medication container.

9. A metered dose inhaler for use in dispensing a dose of a medicament, the inhaler comprising:

an air actuator comprising:

at least one first liquefied gas (LG) expanding volume in a fluid connection with an LG source container via at least one LG inlet, the inhaler further comprising at least one LG outlet;

at least one second air-containing volume fluidly connected to at least one air outlet and to at least one air inlet enabling insertion of air into the at least one second air-containing volume; and a rotor compressor configured for separating said at least one first LG-expanding volume and said at least one second air containing volume such that said LG and said air remain separate at all times, said rotor compressor being adapted to release a flow of compressed air through said at least one air outlet when a predetermined LG pressure has been reached within said at least one first LG-expanding volume; and a nozzle system having at least one nozzle including a nozzle air inlet in fluid communication with said at least one air outlet, a medication inlet in communication with a medication container, a nozzle air-mixture outlet, and a constricted section with a reduced cross-section located between said nozzle air inlet and said nozzle air-mixture outlet;

wherein dimensions of said nozzle system are selected to provide a steady and high velocity of air flow at the nozzle air-mixture outlet, and to provide a particle size of medicament droplets being proportional to the steady and high velocity of the air flow.

10. The inhaler according to claim 9, wherein said nozzle air-mixture outlet is configured with an orifice having one of the following configurations: a diameter of about 0.2 mm to about 0.9 mm; or configured to emit an effective amount of the medicament droplets having an average particle size equal to or less than 5.0 μm.

11. The inhaler according to claim 9, wherein said LG is selected from the following: liquefied petroleum gas (LPG), propane, butane and a combination thereof.

12. The inhaler according to claim 9, wherein said medication container is configured for containing medicament in a form selected from solid form, gas form, liquid form and a combination thereof.

13. The inhaler according to claim 9, wherein said inhaler is portable and handheld.

14. The inhaler according to claim 9, further comprising an LG directing valve configured and operable for activating the LG source container, allowing expansion of said LG in said at least one first LG-expanding volume from its condensed liquid phase to its expanded gas phase, thereby providing that said at least one first LG-expanding volume contains LG compressed between about 20 and about 200 psig; said compressed LG applying a force upon said rotor compressor for compression of said air within said at least one second air-containing volume having predetermined pressure between 3 and about 10 psig, thereby causing release of airflow via said at least one air outlet and providing a metered dose of said medicament droplets having an average size in the range of about 1 μm to about 5 μm inhalable by a user.

15. The inhaler according to claim 9, further comprising a medicament metering valve configured to control a release of a specific amount of medication from the medication container to the nozzle system.

16. The inhaler according to claim 9, wherein said nozzle system further comprises an additional air outlet connected to a backside of the medication container in order to provide additional pressure from the backside of the medication container, thereby accelerating emptying of the medicament droplets from the medication container.

17. A metered dose inhaler for use in dispensing a dose of a medicament, the inhaler comprising:

an air actuator comprising:

at least one first liquefied gas (LG) expanding volume in a fluid connection with an LG source container via at least one LG inlet, the inhaler further comprising at least one LG outlet wherein said at least one air inlet is separate and distinct from said at least one air outlet;

at least one second air-containing volume fluidly connected to at least one air outlet and to at least one air inlet enabling insertion of air into the at least one second air-containing volume;

a piston coupled to the at least one second air-containing volume such that the piston is biased towards the at least one second air-containing volume, the piston being configured for separating said at least one first LG-expanding volume and said at least one second air-containing volume such that said LG and said air remain separate at all times; and a ferromagnetic mechanism in communication with the piston to further control position of the piston along the at least one first LG-expanding volume and the at least one second air-containing volume, said piston being adapted to release a flow of compressed air through said at least one air outlet when a predetermined LG pressure has been reached within said at least one first LG-expanding volume, the flow of compressed air compressing the piston upwards; and a nozzle system having at least one nozzle including a nozzle air inlet in fluid communication with said at least one air outlet, a medication inlet in communication with a medication container, a nozzle air-mixture outlet, and a constricted section with a reduced cross-section located between said nozzle air inlet and said nozzle air-mixture outlet;

wherein dimensions of said nozzle system are selected to provide a steady and high velocity of air flow at the nozzle air-mixture outlet, and to provide a particle size of medicament droplets being proportional to the steady and high velocity of the air flow.

18. The inhaler according to claim 17, wherein said nozzle air-mixture outlet is configured with an orifice having one of the following configurations: a diameter of about 0.2 mm to about 0.9 mm; or configured to emit an effective amount of the medicament droplets having an average particle size equal to or less than 5.0 μm.

19. The inhaler according to claim 17, wherein said LG is selected from the following: liquefied petroleum gas (LPG), propane, butane and a combination thereof.

20. The inhaler according to claim 17, wherein said medication container is configured for containing medicament in a form selected from solid form, gas form, liquid form and a combination thereof.

21. The inhaler according to claim 17, wherein said inhaler is portable and handheld.

22. The inhaler according to claim 17, further comprising an LG directing valve configured and operable for activating the LG source container, allowing expansion of said LG in said at least one first LG-expanding volume from its condensed liquid phase to its expanded gas phase, thereby providing that said at least one first LG-expanding volume contains LG compressed between about 20 and about 200 psig; said compressed LG applying a force upon said piston for compression of said air within said at least one second air-containing volume having predetermined pressure between 3 and about 10 psig, thereby causing release of airflow via said at least one air outlet and providing a metered dose of said medicament droplets having an average size in the range of about 1 μm to about 5 μm inhalable by a user.

23. The inhaler according to claim 17, further comprising a medicament metering valve configured to control a release of a specific amount of medication from the medication container to the nozzle system.

24. The inhaler according to claim 17, wherein said nozzle system further comprises an additional air outlet connected to a backside of the medication container in order to provide additional pressure from the backside of the medication container, thereby accelerating emptying of the medicament droplets from the medication container.

* * * * *